(12) United States Patent
Rosenthal et al.

(10) Patent No.: US 6,485,872 B1
(45) Date of Patent: Nov. 26, 2002

(54) METHOD AND APPARATUS FOR MEASURING THE COMPOSITION AND OTHER PROPERTIES OF THIN FILMS UTILIZING INFRARED RADIATION

(75) Inventors: Peter A. Rosenthal, West Simsbury; Sylvie Charpenay, Vernon; Victor A. Yakovlev, West Hartford, all of CT (US)

(73) Assignee: MKS Instruments, Inc., Andover, MA (US)

(*) Notice: Subject to any disclaimer, the term of this patent is extended or adjusted under 35 U.S.C. 154(b) by 65 days.

(21) Appl. No.: 09/718,602

(22) Filed: Nov. 22, 2000

Related U.S. Application Data
(60) Provisional application No. 60/168,974, filed on Dec. 3, 1999.

(51) Int. Cl.[7] .................................................. G03C 5/00
(52) U.S. Cl. ........................ 430/30; 430/944; 250/472.1; 250/473.1; 250/474.1
(58) Field of Search ................. 430/30, 944; 250/472.1, 250/473.1, 474.1

(56) References Cited

U.S. PATENT DOCUMENTS

| | | | |
|---|---|---|---|
| 4,905,170 A | 2/1990 | Forouhi et al. ............. 364/556 |
| 5,403,433 A | 4/1995 | Morrison et al. ........... 156/626 |
| 5,595,916 A | 1/1997 | Fujimura et al. .............. 437/8 |
| 5,604,581 A | 2/1997 | Liu et al. ...................... 356/73 |
| 5,666,200 A | 9/1997 | Drevillon et al. ........... 356/368 |
| 5,706,212 A | 1/1998 | Thompson et al. ......... 364/525 |
| 5,900,633 A | 5/1999 | Solomon et al. ....... 250/339.08 |

*Primary Examiner*—Christopher G. Young
(74) *Attorney, Agent, or Firm*—Ira S. Dorman

(57) ABSTRACT

The composition, free carrier concentrations, and other properties of thin films and graded layers embedded in film stack structures are measured by the method of the invention, which is based upon the application of two novel algorithms to extract the composition of a measured layer independently of the confounding effects of additional layers, and which can be effected even when calibration samples are not available with the same layered structure as the samples to be measured. The method uses sample model-based analysis algorithms to extract the dielectric function of the layer to be measured, combined with model-based analysis to relate the composition of the layer to its dielectric function. Because the dielectric function of a layer is a bulk spectral property of the material, and is inherently independent of the thickness of the layer, the composition of the material can be determined more easily and unambiguously from its dielectric function than from raw spectral quantities such as reflectance, ellipsometry, and transmittance, which spectral data are influenced strongly by the optical properties of the overlayers, the underlayers, and the substrate material. The method enables the measurement of layer composition with significantly fewer calibration samples, it allows product wafer analysis with structures that are significantly more complicated than the calibration samples, and it is intrinsically more reliable for transferring calibrations between tools even when the measurement geometry varies from tool-to-tool.

32 Claims, 12 Drawing Sheets

METHOD AND APPARATUS FOR MEASURING THE COMPOSITION AND OTHER PROPERTIES OF THIN FILMS UTILIZING INFRARED RADIATION

CROSS-REFERENCE TO RELATED APPLICATIONN

The present application claims the benefit of U.S. Provisional Application No. 60/168,974 filed Dec. 3, 1999 in the names of the present inventors.

STATEMENT REGARDING FEDERALLY SPONSORED RESEARCH OR DEVELOPMENT

The United States Government has rights in this invention pursuant to National Science Foundation Contract No. DMI-9860798.

BACKGROUND OF THE INVENTION

Many current processes for manufacturing microelectronic devices, and the like, entail the fabrication of stacks of thin films having compositions that must be controlled to satisfy exacting standards and extremely tight tolerances. For example, fluorinated silica glass (FSG) films are used as dielectric layers in semiconductor integrated circuits (IC's); because the fluorine constituent serves to reduce the dielectric constant of the layer, and thereby to improve circuit speed and reduce cross-talk between wires, it is important to control its concentration so as to optimize the electrical, chemical, and other properties of the layer. Similarly, the dopant concentrations in boron- and phosphorus-doped silica glass (BPSG) films, which are used as intermetal dielectrics, are quite critical and must be monitored and controlled carefully to maintain high yields in production, and the same is true of many of the newer materials that are now being employed as thin films, which materials tend to be compounds with complex chemical compositions and interfaces that must be monitored and controlled.

It is now also common for integrated circuits to include complex submicron geometric structures. For example, dynamic random access memory (DRAM) devices are typically formed with deep, tapered trenches etched into the silicon to thereby provide larger area capacitors without increasing the chip surface area utilized. The sidewall taper angle and depth of such trenches must be controlled carefully to maintain yield; moreover, the formed trenches may themselves be filled subsequently with materials such as dielectrics and polysilicon, giving rise to the need for yet further process monitoring and control capability.

In addition to the foregoing, compositionally graded structures are often employed in thin film manufacturing; dopants are typically diffused or implanted into semiconductor devices to provide diffuse composition profiles; and silicon on insulator (SOI) wafers are commonly fabricated by forming a buried oxide layer with a graded composition profile, which must be sharpened by thermal annealing. Controlling the depth profiles of such structures is of critical importance.

In all of the processes referred to, as well as in others that will be evident to those skilled in the art, it is necessary to measure the properties and characteristics of at least one layer of interest. Typically, and for any of a number of reasons, such measurements cannot presently be performed directly on the product wafers: i.e., product wafers with patterns, and multilayered film stacks, are often too complex for practical data analysis; measurements are often either destructive to the sample or are such that they pose a significant risk of contamination or defect introduction; and current techniques, carried out in the visible and ultraviolet wavelength ranges, are not sufficiently sensitive to enable accurate measurement of crucial layer properties, such as composition and carrier concentration. In any event, non-destructive measurement techniques will usually be preferred, largely because they enable the use of in-line process control methodologies without undue consumption of expensive, non-product test wafers.

SUMMARY OF THE INVENTION

Accordingly, broad objects of the present invention are to provide a novel method and apparatus for measuring and controlling the composition and other properties of thin films, in accordance with which at least certain of the limitations and deficiencies of current techniques and procedures, as described herein, are minimized, avoided and/or overcome.

It has now been found that certain of the foregoing and related objects of the invention are attained by the provision of a method for estimating at least one parameter of a sample, determined from the dielectric function of a material of which at least one layer of the sample consists. The method comprises the steps:

(a) providing a sample comprised of at least one layer and having a substantially specular surface;

(b) defining an optical model of the sample along a direction perpendicular to its surface and based upon reflectance values, the "at least one layer" being defmed in the model by a thickness value and, for each of a multiplicity of wavelengths in the infrared spectral region, by a dielectric function value;

(c) providing a training set consisting of measured values of the "at least one parameter" and an associated dielectric function, the measured values being obtained from a multiplicity of samples selected to represent a range of values of the at least one parameter;

(d) determining from the training set a predictive mathematical relationship between the at least one parameter and the associated dielectric function, so as to enable prediction of the at least one parameter from input values of dielectric function;

(e) irradiating the specular surface of the sample with infrared radiation, including the multiplicity of wavelengths referred to in step (b), and obtaining a measured reflectance spectrum composed of values obtained over the multiplicity of wavelengths;

(f) simulating a reflectance spectrum from the optical model at the multiplicity of wavelengths using various values of the dielectric function calculated from assumed dielectric function descriptors and a value of the thickness of the at least one layer, and computing the various values of the dielectric function descriptors so as to minimize the difference between the simulated reflectance spectrum and the measured reflectance spectrum, thereby determining an optimized dielectric function value for the at least one layer at the multiplicity of wavelengths; and (g) calculating the value of the at least one parameter using the optimized dielectric function value and the predictive mathematical relationship.

In certain preferred embodiments a pattern of variation derived from the training set is utilized so as to constrain the number of the descriptors required to describe the dielectric function. The values of dielectric function used may be parametrized as weighted linear superpositions of vectors determined to span the space of dielectric functions derived from the training set, with the descriptors being the coefficients of the vectors. At least one of the vectors will desirably be determined through a multivariate statistical regression of the set of dielectric functions measured in creating the training set. The predictive mathematical relationship may for example be determined through a multivariate statistical regression of the training set; it may be determined employing a neural network algorithm calibrated with the training set; or it may be determined by establishing a library of dielectric function values with associated values of the at least one parameter, organized in the form of a look-up table which is accessed to determine the parameter from the optimized values, and access may include the additional step of interpolating between elements thereof. The predictive mathematical relationship may be established between the at least one parameter and spectral features derived from the dielectric function of the training set. The spectral feature may be at least one characteristic of at least one peak observed in the training set dielectric function, such a characteristic typically being the intensity, position, height or width of the at least one peak. In certain instances the thickness value will be varied in step (f) as well as using the computed values of the dielectric function descriptors.

The at least one parameter calculated by the present method may represent the species and/or the concentration of at least one chemical constituent of the material of the at least one layer. In particular, the parameter may be the concentration of fluorine atoms within the material, the concentration of hydroxyl groups within a dielectric matrix, the concentration of water molecules within a dielectric matrix, the concentration of hydrogen atoms within a dielectric matrix, or the concentrations of at least one of boron, phosphorus, and germanium in the at least one layer. When the at least one layer contains barium, strontium and/or titanium atoms, the parameter may be the concentration thereof. Additionally, the parameter value calculated may represent the stress in the at least one layer, the density of crystal defects therein, or a porosity characteristic thereof, which characteristic may describe the pore size distribution or the total fractional pore volume within the layer. Furthermore, the value determined may be characteristic of a lithography process, in instances in which the layer of interest comprises a lithographic resist layer, with the parameter representing the exposure dose of the lithographic resist layer, a critical dimension obtained after completing a lithography process step on the sample, or a measure of the sidewall profile obtained following such a process step. In instances in which the one layer is a compound semiconductor composed of at least three chemical elements, the parameter may be representative of the relative ratios of the elements, such elements generally being selected from the group consisting of Si, Ge, Al, Ga, As, N, P, In, C, Sb, Zn, Hg, Cd, B, and Te. Finally, the at least one parameter may be representative of the electrical dielectric constant of the analyzed layer.

Other objects of the invention are attained by the provision of apparatus for estimating at least one parameter of a sample, determined from the dielectric function of a material of which at least one layer of the sample consists. The apparatus comprises means for irradiating a surface of a sample with infrared radiation, including each of multiplicity of wavelengths in the infrared spectral region, and for obtaining a measured reflectance spectrum composed of values obtained over the multiplicity of wavelengths; and electronic data processing means. The data processing means of the apparatus is programmed to:

(a) define an optical model of the sample along a direction perpendicular to a surface thereof and based upon reflectance values, the at least one layer of the sample being defined in the model by a thickness value and, for each of a multiplicity of wavelengths in the infrared spectral region, by a dielectric function value;

(b) provide a training set consisting of measured values of the at least one parameter and an associated dielectric function, the measured values being obtained from a multiplicity of samples selected to represent a range of values of the at least one parameter;

(c) determine from the training set a predictive mathematical relationship between the at least one parameter and the associated dielectric function, so as to enable prediction of the at least one parameter from input values of dielectric function;

(d) simulate a reflectance spectrum from the optical model at the multiplicity of wavelengths using values of the dielectric function calculated from various dielectric function descriptors and a value of the thickness of the at least one layer, and to compute the values of the dielectric function descriptors so as to minimize the difference between the simulated reflectance spectrum and the measured reflectance spectrum, thereby determining an optimized dielectric function value for the at least one layer at the multiplicity of wave-lengths; and (e) calculate the value of the at least one parameter using the optimized dielectric function value and the predictive mathematical relationship.

As a practical matter, the invention relates to the measurement and control of layer and interface properties of thin films fabricated during the manufacture of microelectronic devices, solar conversion devices, magnetic storage devices, and the like, enabling the control of such properties and of such manufacturing operations. It provides a new approach for measuring layers deposited in thin-film structures of both present and also anticipated constructions, and it enables measurements of layers in relatively complex structures, such as multilayered film stacks. The method does not require calibration to be performed on the same measurement system as that which is present in a tool by which the method is to be implemented, and calibration samples can be relatively simple; for example, they may comprise a set of films covering a range of composition, all deposited on inexpensive, unpatterned silicon substrates. As will be appreciated, once the calibration has been performed using the calibration samples, actual measurements can be carried out on metallic substrates, multilayered configurations, or other more complicated structures.

The method and apparatus of the invention exploit a number of unique capabilities associated with infrared measurement techniques. In particular, the optical constants of most materials encode a great deal of chemical composition information that is unavailable in the UV and visible ranges. The longer wavelengths of infrared light also allow specular measurements on many patterned samples, whereas the scattering and diffraction of UV and visible probing beams, caused by patterns and layer roughness, often preclude accurate specular measurements. In addition, the infrared dielectric function is a complex spectral quantity which encodes information about the absorption and index of refraction of a material, as a function of optical frequency, and most materials have characteristic dielectric function signatures, in the infrared, that are related to their composition. The present invention enables the extraction of information indicative of the composition of a given layer, by computing its dielectric function from optical measurements, and at the same time eliminates confounding effects of other layers and substrate materials present in the structure; chemometric compositional analysis of the dielectric function can then be performed effectively.

One advantage of the instant approach resides in the correlation that it provides between the composition of a material and its dielectric function, which correlation does not depend upon details of the measurement geometry employed, e.g., the angle of incidence or the polarization of the probe beam. Optical properties, such as reflectance and transmit-tance, do on the other hand depend strongly upon the characteristics of the probe beam.

It is know that infrared reflectometry can be employed to extract layer composition (see J. E. Franke, T. M. Niemczyk, and D. M. Haaland, "Infrared spectroscopic techniques for quantitative characterization of dielectric thin films on silicon wafers" Spectrochimica Acta. Wol. 50A, No. 10. Pp 1687–1723, 1994 Elsevier Science Ltd. U.K.). However, in the methodology described the chemometric compositional analysis algorithm is applied directly to the reflectance, which not only limits the range of allowable sample thicknesses to that which is provided in the calibration sample set, but also requires the training set to constitute a relatively large number of sample thicknesses (as well as compositions) to accommodate measurements over widely varying thicknesses. Thus, the method of Haaland (and other current methods) permits measurements to be made only on samples comprised of a substrate and film stack structure that is essentially identical to that which constitutes the calibration training set. By applying chemometric analysis to the dielectric function (DF), on the other hand, which can be extracted from the reflectance in accordance with the present invention, the foregoing shortcomings are eliminated and calibration of the analysis system is enabled using much simpler, and much smaller, training sets.

More specifically, because the DF deconvolution removes from the chemometric model the influences of other variables, such as are attributable to the substrate and to the thickness of the layers, the training set need not span a wide range of film thicknesses and it can constitute relatively few members. Also, because the deconvolution process eliminates the effects of other layers that may be present thin films deposited in more complicated structures, such as on metal or dielectric underlayers, can be analyzed using an established calibration model; i.e., no new set of training samples is required. And finally, because the DF deconvolution eliminates any influence that the angle of probe beam incidence might have upon the spectral data obtained, measurements can be performed using a measurement geometry that is radically different from that which is employed to generate the calibration data.

DETAILED DESCRIPTION OF THE PREFERRED EMBODIMENTS

Figure 15:
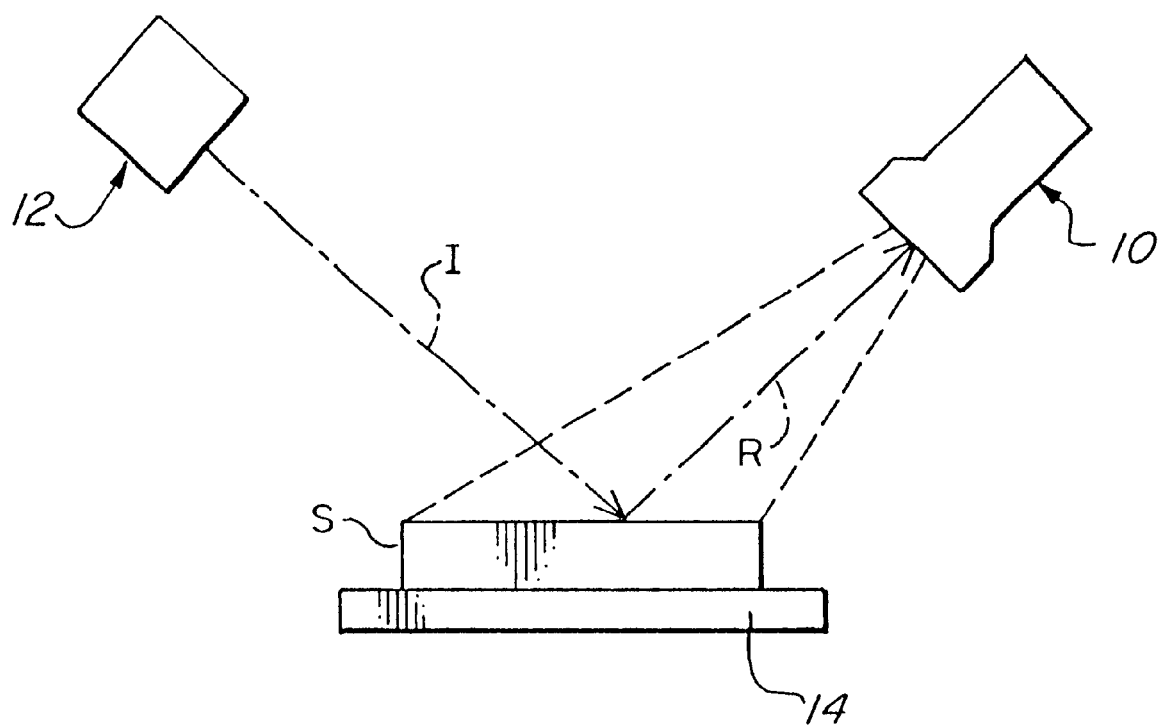
FIG. 15 is a diagrammatic representation of apparatus embodying the invention.

The apparatus of the invention is diagrammatically illustrated in FIG. 15, and consists fundamentally of a detector and electronic data processing means, generally designated by the numeral 10, and an infrared radiation source, generally designated by the numeral 12. The incident beam I from the source 12 is directed toward the surface of a sample S, supported on a stage 14, and reflected radiation R is detected and processed, in accordance with the description herein set forth, by the detector/data processing means 10. Specific features of such apparatus will be apparent to those skilled in the art from the information provided, and need not therefore be explained in further detail.

In accordance with the present invention, the training set will preferably include a sufficient number of samples to adequately characterize the variation of the layer properties as a function of input parameters, which parameters will typically be indicative of the concentration of one or more components of the composition. More generally, however, the parameters may be indicative of variables such as crystallinity, mobility, strain, defect density, etc. In those instances in which the subject layer is a patterned test structure, the parameters that are varied in the training set may most appropriately be linewidth, thickness, sidewall taper angle, and/or other microstructural properties.

Any of numerous approaches can be employed for determining the dielectric function of a layer. If optical methods are utilized however, as is preferred, a reflectance, transmission, or ellipsometry measurement will typically be performed on the sample, with the measured data being analyzed mathematically to extract the dielectric function using algorithms such as a Kramers Kronig inversion, the so-called sum-of-Lorentzian method taught in Morrison et al. U.S. Pat. No. 5,403,433, and other similar parametric model-based analysis techniques. Such algorithms allow extraction of the wavelength-dependent dielectric functions from optical measurements, such as reflectance, transmittance, or ellipsometry. The DF deconvolution explicitly eliminates from the data the effects of layer thickness, substrate properties, and of other layers present in the structure, effectively isolating the properties of the subject layer from such confounding influences.

The DF deconvolution procedure described in the above-identified Morrison et al. patent provides another useful parametrization of the DF that can also be analyzed according to the present invention. In accordance with the Morrison et al. approach, the dielectric function $\epsilon(v)$ is decomposed into a basis set of narrow, equally spaced Lorentzians of equal width, as shown in Equation 1, which follows:

$$\varepsilon(v) = \varepsilon_\infty + \sum \frac{A_k}{v_k^2 - v^2 - iv\gamma}$$

in which the values $v_k$ are defined to be equally spaced by some small increment, i.e. $v_k = v + k\delta v$, and wherein the values $A_k$ can be related directly to the density of chemical bonds with resonant absorptions at the frequency $v_k$. Other approaches to extraction of the dielectric function include Kramers Kronig analysis, ellipsometric analysis, multiangle reflectometry, etc.

After the DF has been extracted, the next step is to relate the spectral features of the DF to the composition of the layer, for which step there are also several alternative approaches. For example, a multivariate model that relates the sample parameters to measured spectra can be constructed using a suitable chemometric algorithm such as classical least squares, inverse least squares, partial least squares, or principal component or factor analysis. All of these methods are based upon the construction of an analysis model using a regression analysis of a training set.

One approach to relating the DF to the sample parameters, in accordance with step (d), is to employ knowledge of the optical properties of the material in question to identify the spectral regions of the DF that encode particular compositional information. For example, it is known that hydroxyl groups have a strong absorption band lying between about 3000 and 3500 cm$^{-1}$. The amplitude of the dielectric function within that range may therefore be related to the —OH concentration in a film through correlation with independent knowledge of the —OH concentration obtained either by independent measurements or through knowledge of the fabrication process. This approach allows heuristic knowledge of the layer chemistry to be used in the construction of the model.

A second, more general approach for relating the DF to the sample parameters applies a statistical discipline, such as principal component analysis, to characterize the variation of the DF spectra, extracted from the training set in terms of so-called scores and loading vectors. This approach enables the rigorous construction of a vector space that spans the observed variation of the training set using relatively few degrees of freedom, and enables a dielectric function to be represented as a linear combination of independent vectors, weighted by a particular set of scores. The approach provides the considerable advantage of allowing prediction of the dielectric function using a statistically optimized minimal number of parameters and without requiring first-principles models to construct the model for DF prediction.

After calibration of the DF-prediction model, using the training samples, an unknown sample to be analyzed is measured in accordance with step (e). Preferred methods for measurement are infrared reflectometry, ellipsometry, and variations of those basic techniques; the basic techniques and the variants thereof are referred to herein and in the appended claims by the general terms "reflectance," "reflectometry," and the like. The layer stack structure of the sample must be known, but it need not have the same layer sequence as that which is provided in the training set.

In step (f) a predictive model is constructed that can predict the measured data of a structure of the type supplied in step (e), using the model developed in step (b) and employing assumed values of the unknown layer parameters in order to compute the DF of the unknown layer. Any additional layers present in the structure can be treated in the same way, using different DF models previously computed from other training sets, or they can be treated using other physical models, such as those that are described in Liu et al. U.S. Pat. No. 5,604,581, to predict the DF of each additional layer. Similar procedures are applied to predict the DF of the substrate as well.

In addition to determining the DF of every layer in the structure, other parameters (e.g. layer thicknesses) that are needed to predict the measured data are defined in step (f). Once the thicknesses and DF parameters of each layer are defined in the model, multilayered optical calculations, based on Maxwell's equations, can be used to predict reflectance, ellipsometry parameters, and other measured properties of the layer stack. The transfer matrix method described by Liu et al. to calculate the reflectance from the dielectric functions and thicknesses of the layer stack is an example of this approach. Other parameters of the model that relate to the measurement configuration can also be defined, such as the angle of incidence and/or the polarization of the probing beam, etc.

The reflectance analysis of a fluorinated silica glass film on a silicon substrate provides an example of the implementation of step (d). Inputs to the model are the fluorine concentration, the film thickness, and the substrate carrier concentration. The DF model, previously constructed from the analysis of a training set of FSG films of different fluorine concentrations, would be employed to compute the DF of the layer based upon its assumed fluorine concentration. The reflectance of the sample would thus be predicted from assumed values of the layer thickness, substrate doping, and fluorine concentration, using a transfer matrix method analogous to that described in the above-identified Morrison et al. and Liu et al. patents.

Step (f) may be carried out using an iterative regression analysis, in accordance with which a set of assumed input parameters for the model of step (b) are varied in order to best fit to the measured data to the data predicted by the model. A subset of the parameters defined in step (b) may be held fixed, at assumed values, during the fit.

Finally, in accordance with step (g) the predicted parameters are reported as the measurement results. A "goodness-of-fit parameter," quantifying the degree of agreement between the predicted and measured data, may also be reported to characterize the quality of the measurement.

Illustrative of the efficacy of the method of the invention are the following examples:

EXAMPLE ONE

Compositional Analysis of a Single Layer of BPSG on a Silicon Substrate

In this Example the method of the invention is applied for the determination of the composition of a thin film; specifically, a boro-phospho-silica glass (BPSG) film, deposited on a silicon substrate, is analyzed using the seven-step methodology described above.

First, a training set of BPSG films, ranging up to approximately one micron thick, were deposited on silicon substrates (step (c)); the concentrations of boron and phosphorus in the training set spanned a range from pure $SiO_2$ (i.e., no boron or phosphorus) to levels of about 8 percent by weight of the elements.

The mid-infrared reflectance spectrum of each sample in the training set was measured and a DF deconvolution was performed, using the method of Morrison et al., to determine the dielectric function of each layer. It will be appreciated that ellipsometry, or combined reflectance and transmittance measurements followed by appropriate numerical analysis, may alternatively be employed to extract the DF of the film for each sample constituting the training set.

These dielectric functions, together with the independently provided nominal boron and phosphorous concentrations of the training set samples, comprised a training data set. A principal component analysis was then performed, using the training data set dielectric functions as inputs. This procedure generates a set of loading vectors and scores constructed such that the dielectric function of each sample in the training set can be well approximated by a weighted linear sum of loading vectors. Each sample is distinguished by its weighting coefficient, while the loading vectors are common to the samples in the training set. The boron and phosphorous concentrations of the samples are in turn represented as a function of the scores, with this function also common to the training set and the particular details of the principal component.

Given an unknown sample, the measurement process then reduces to determining its dielectric function, fitting the dielectric function as a linear sum of loading vectors, and then taking the appropriate function of the scores to compute the boron or phosphorous composition. One approach to determining the dielectric function of the unknown sample is to perform a "sum of Lorentzian" (Morrison et al,) or Kramers-Kronig decomposition of the reflectance data. Another approach is to perform an iterative fit of the reflectance in which the dielectric function of the BPSG layer is represented as an unknown linear sum of loading vectors derived from the training set. The unknown scores are adjusted during the fit to best match the modeled reflectance data to the measured data. Of course it should be appreciated that other parameters such as layer thicknesses and dielectric function parameters of other layers in the structure may be fitted following this procedure as well.

Following this procedure, a set of fourteen samples was employed to generate loading vectors and to cross-validate the predictive model. The fourteen samples were separated into an "unknown sample" and a training set of thirteen samples. The training set was analyzed to determine a set of five loading vectors. The reflectance of the fourteenth "unknown sample" was then fitted for its dielectric function. The dielectric function was then fitted as a linear sum of the five loading vectors and the boron and phosphorous concentrations were computed from the scores obtained. This process was repeated systematically with each sample in the set getting treated in turn as an unknown sample, using the model derived from the other thirteen samples to predict the unknown's composition.

Figure 11:
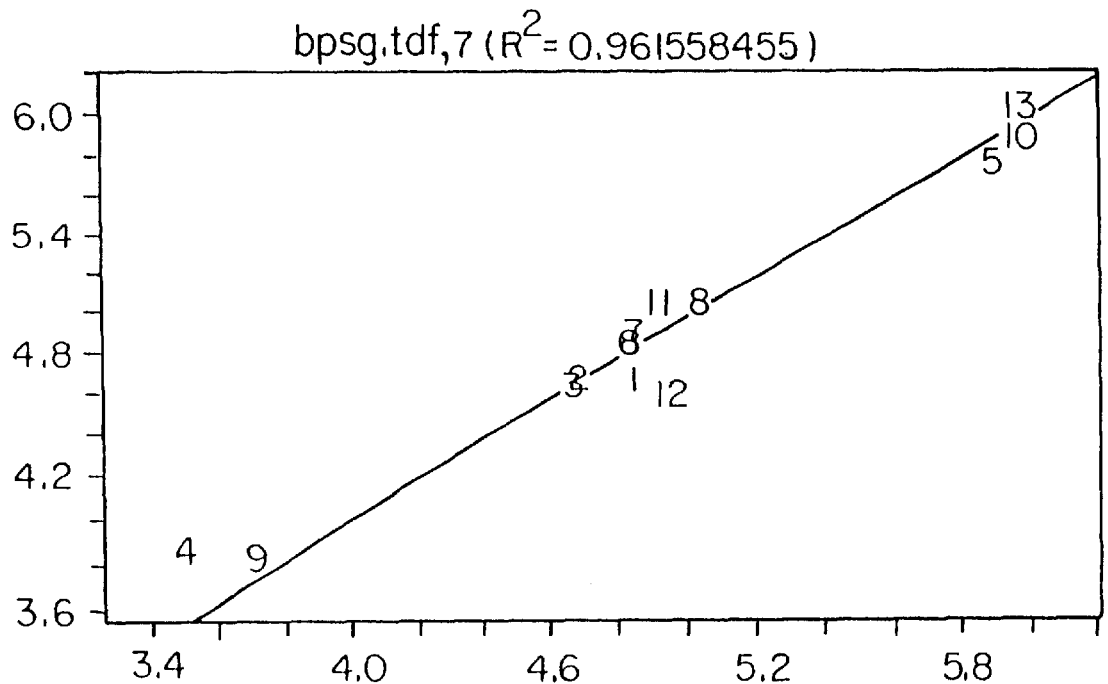
FIGS. 11 and 12 are cross-validation scatter plots for phosphorous and boron measurements, respectively; in each instance the vertical axis shows the concentration of the element in a training set, as predicted by a multivariate model, and the horizontal axis shows the nominal concentration of the element provided with the training set.
Figure 12:
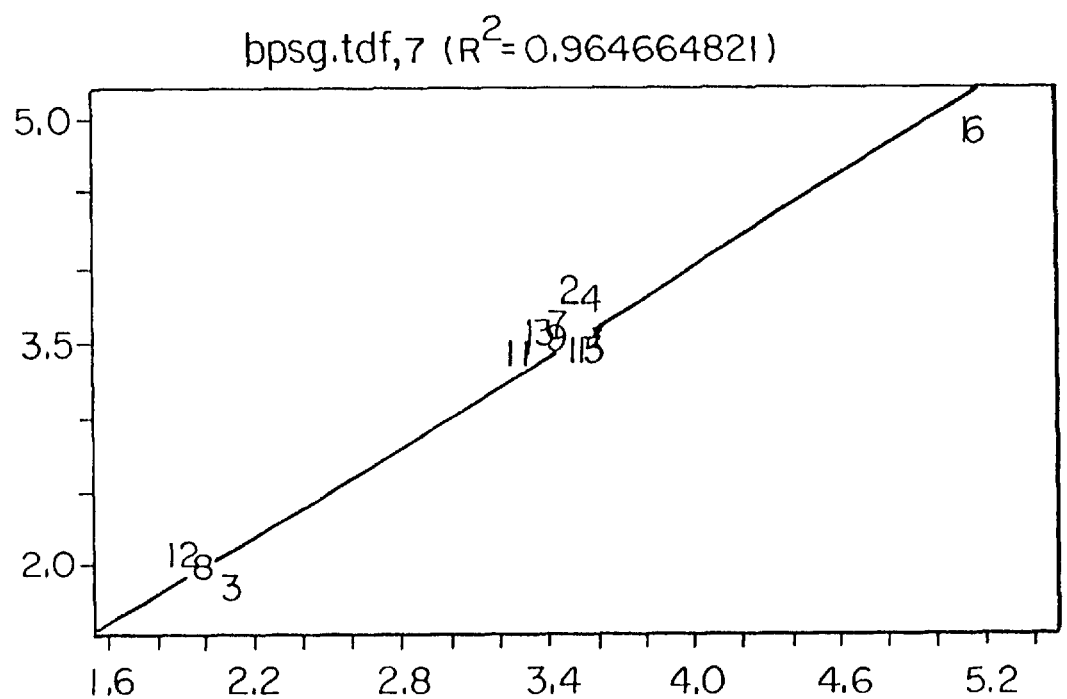

The results of this cross-validation procedure can be presented in the form of scatter plots in which the vertical axis represents the predicted value of the boron or phosphorous concentration, and the horizontal axis represents the nominal values of the boron or phosphorous concentrations provided with the training data set. The results of this cross-validation of the model are summarized in the scatter plots of FIGS. 11 and 12. As can be seen, the model predicted excellently the boron and phosphorous concentrations of the samples in the training set.

EXAMPLE TWO

Analysis of Composition of a BPSG Layer Deposited on a Doped Silicon Substrate

This Example illustrates a layer analysis in which the fitting model employs fitting parameters that relate to structures other than the BPSG in question. The approach is similar to that of Example One; however, a sample of unknown boron and phosphorus composition, unknown thickness, and unknown substrate carrier concentration is measured using an infrared reflectometer.

In step (f) a fitting model is was employed in which the unknown parameters were boron concentration, phosphorus concentration, BPSG layer thickness, and substrate carrier concentration. The substrate dielectric function was modeled as a function of carrier concentration using a Drude model, as in the Liu et al. patent referred to above. The DF of the BPSG layer was modeled as a sum of loading vectors or Lorentzians, using the same method employed in the previous Example, and the reflectance was modeled using the transfer matrix formalism described in the referenced Morrison et al. patent.

The modeled reflectance was iteratively fit to the measured data by varying the model-fitting parameters. As will be appreciated, if parameters such as the film thickness are known independently, through means such as visible wavelength reflectometry analysis, they may of course be held fixed at their nominal values. One again, the final values of boron and phosphorus concentrations, and any other fitting parameters and goodness-of-fit numbers determined, are reported in step (7) as the measurement results. In this Example, the optical effects of the substrate doping upon the reflectance do not interfere with the determination of the BPSG properties, because the fitting model explicitly accounts for the substrate doping effects.

EXAMPLE THREE

Analysis of Fluorine Doped Silica Glass

Figure 1:
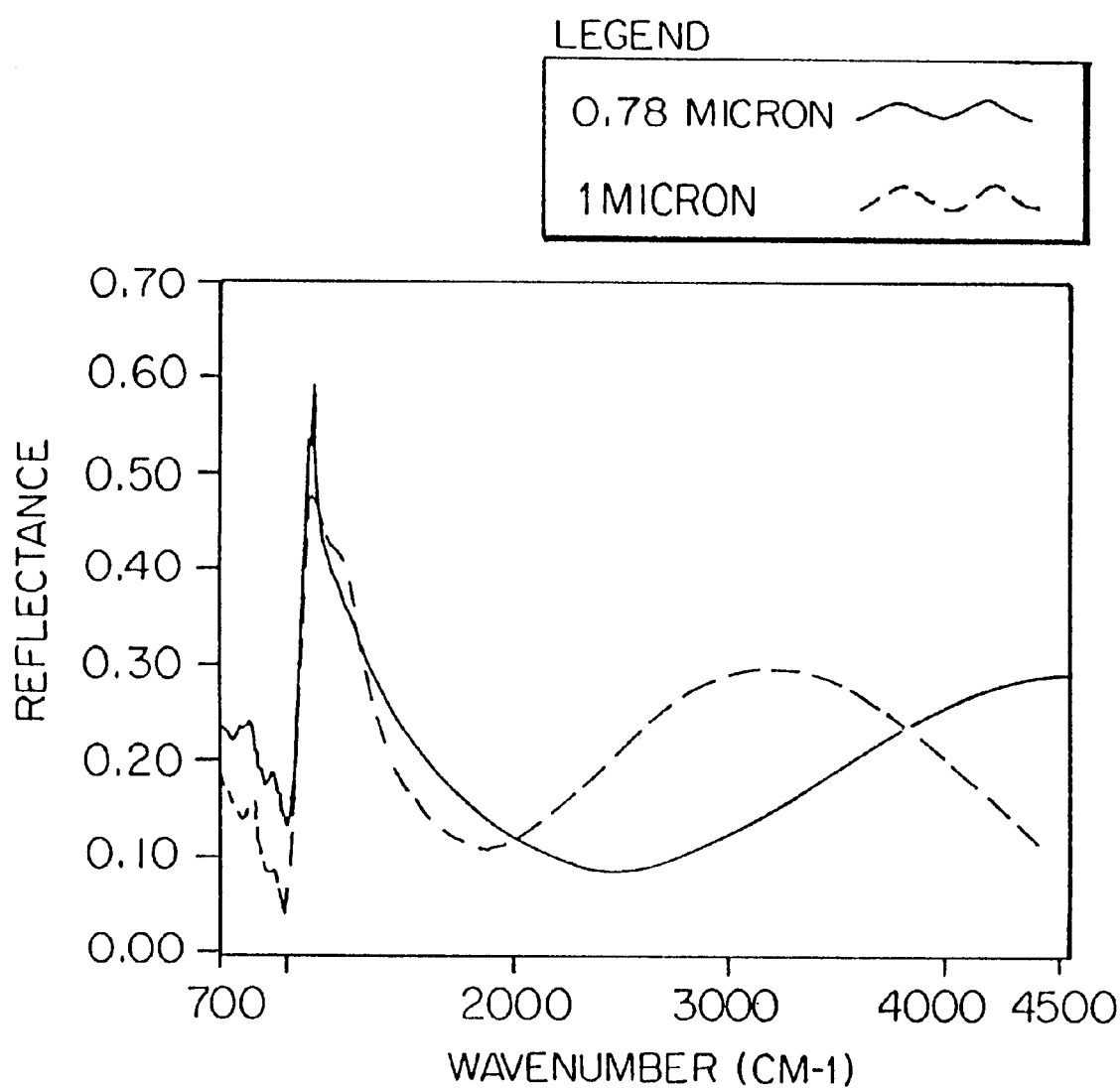
FIG. 1 is a plot of curves showing measured reflectance spectra for two films of fluorine-doped glass of different thickness, namely, 0.78 µm and 1 µm.
Figure 2A:
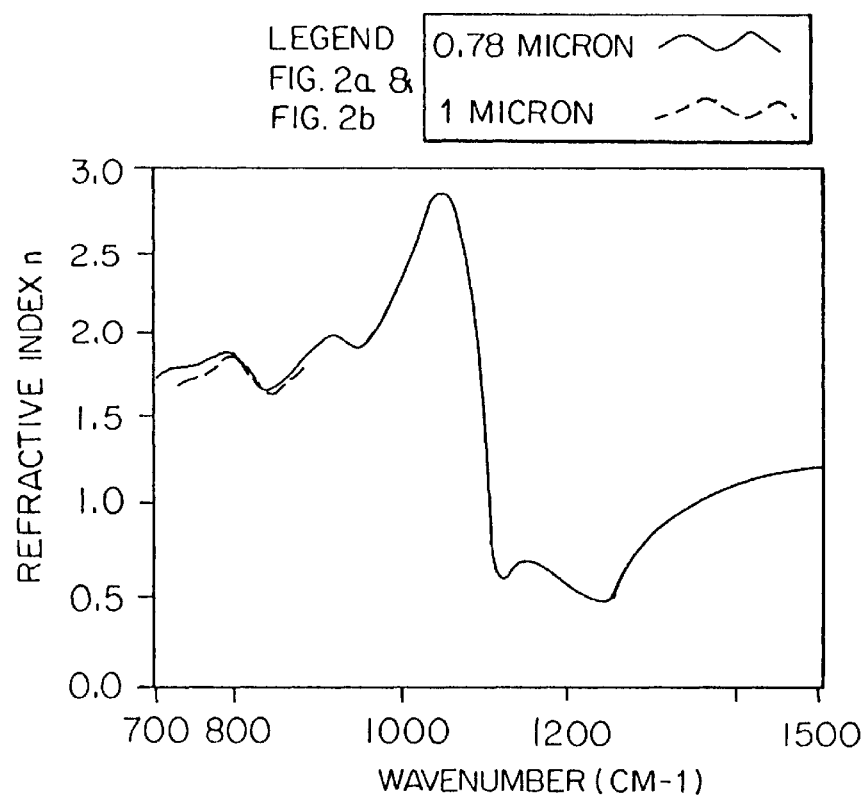
FIG. 2 comprises plots of curves showing the extracted dielectric functions for the two films of FIG. 1, wherein plot (a) shows the refractive indices n and plot (b) shows the extinction coefficients k.
Figure 2B:
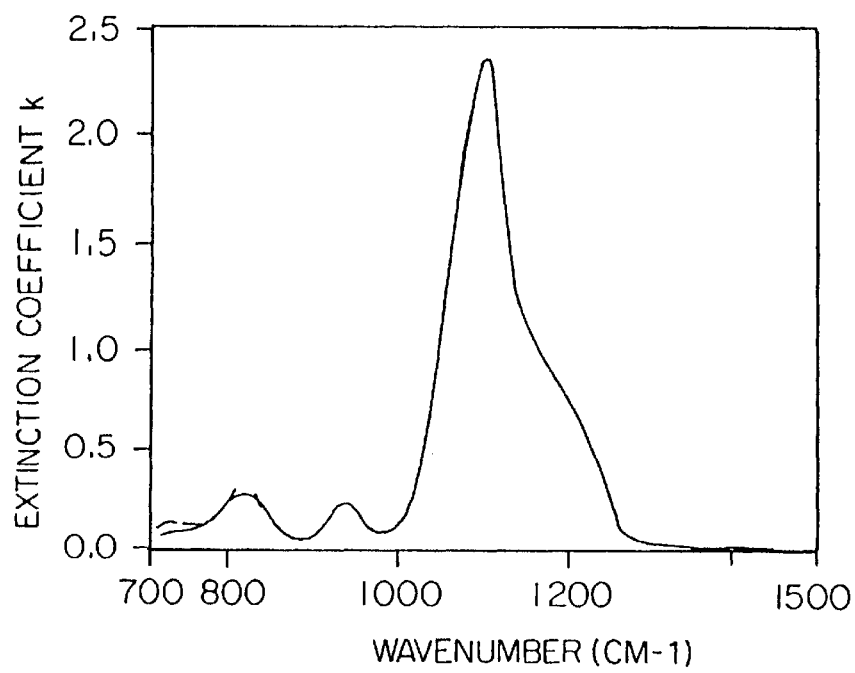
Figure 3:
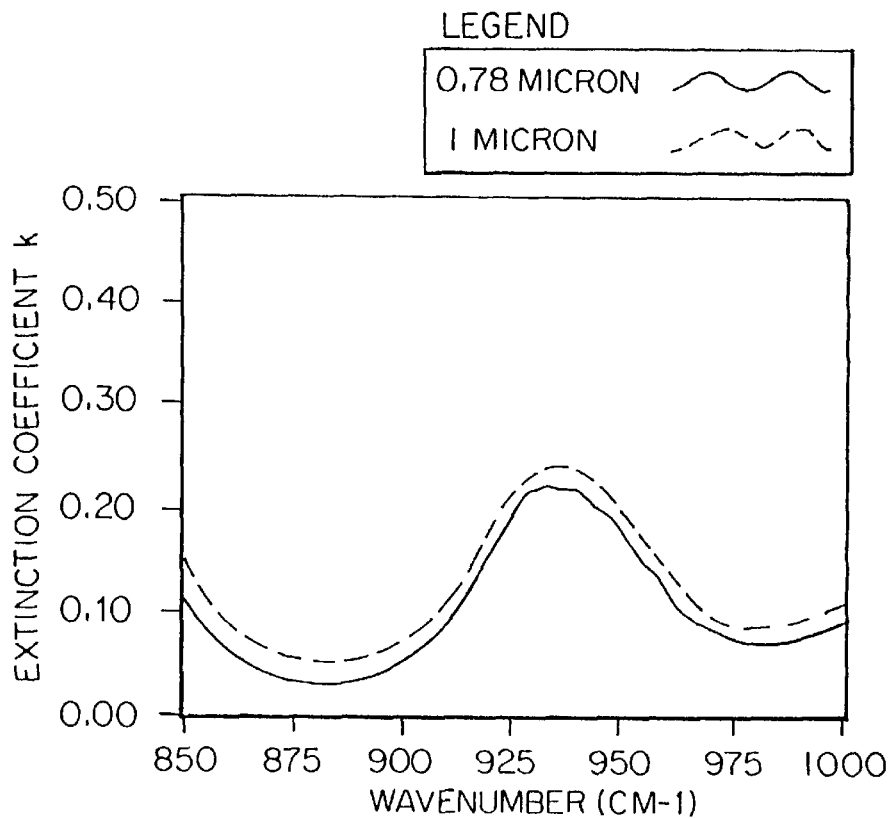
FIG. 3 is a plot of curves showing detailed regions of the extinction coefficients k around the Si—F chemical absorption at 930 cm$^{-1}$.
Figure 4:
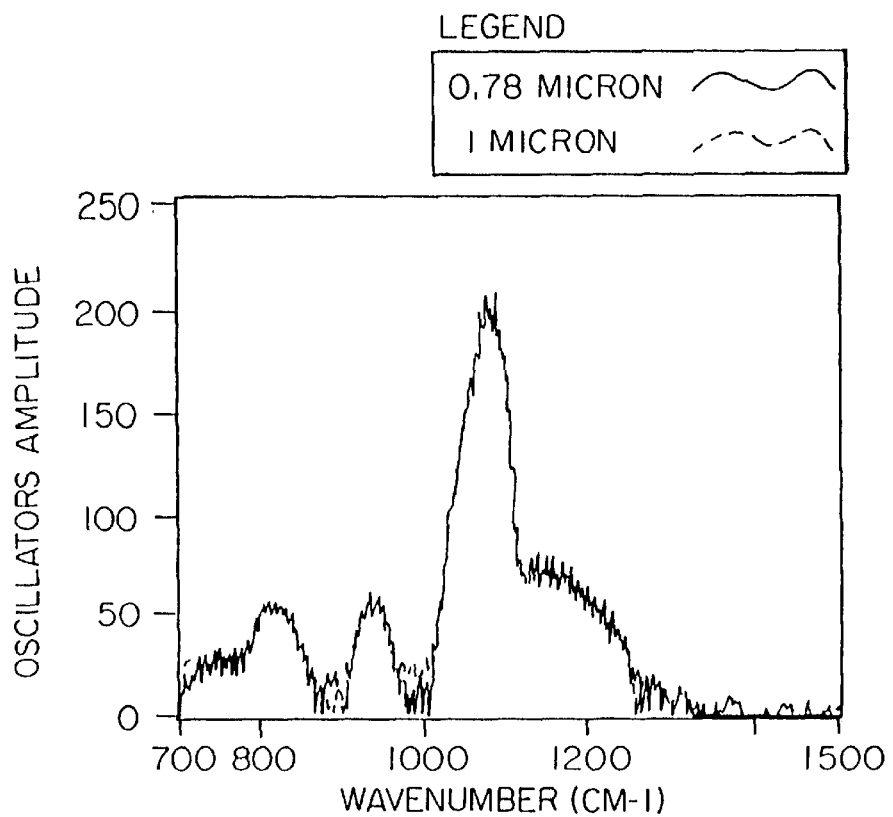
FIG. 4 is a plot of curves showing oscillator amplitudes for the two films.
Figure 5:
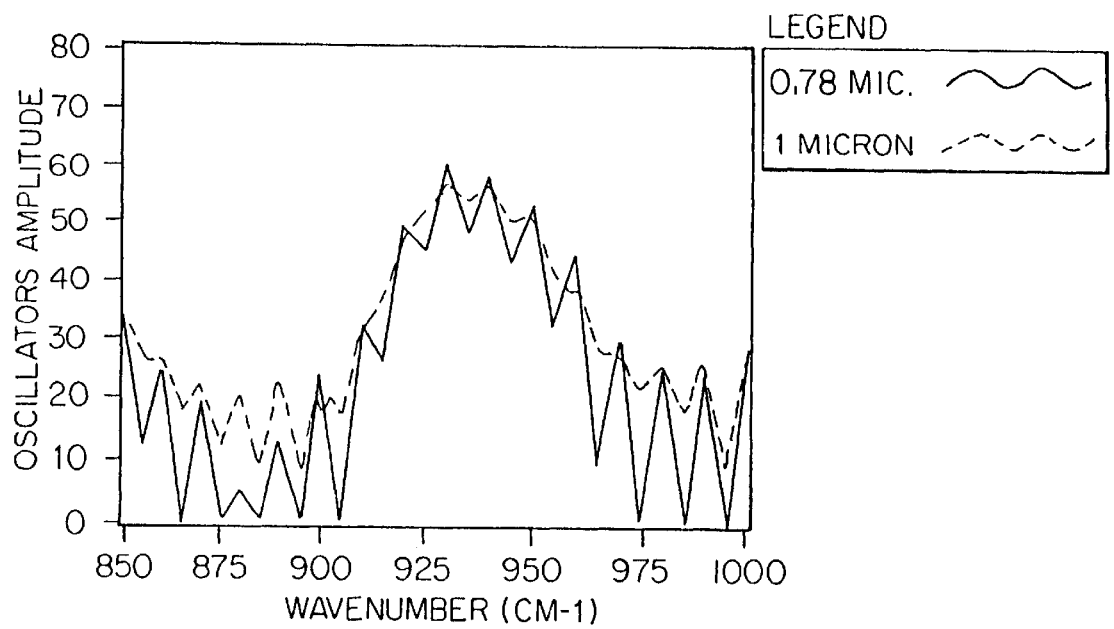
FIG. 5 is a plot of curves showing detailed regions around 930 cm$^{-1}$ for the oscillator amplitudes shown in FIG. 4.

Reference to FIGS. 1 through 5 provides graphic illustration of step (2) of the present method. As noted, FIG. 1 shows the measured reflectance of two films of fluorine-doped silica glass (FSG) having similar compositions but different nominal thicknesses, it being seen that the reflectance spectra vary from one another due to the thickness-related effects of the interference fringe and absorption bands. FIG. 2 shows the dielectric function spectra for the same two films, extracted using the method of Morrison et al., and FIG. 3 provides greater detail as to the region of the spectrum around 930 wavenumbers where the Si—F chemical absorption is observed; it is noted that the dielectric functions of the two films are nearly identical, even though the layer thickness and reflectance spectra are significantly different. FIG. 4 shows the oscillator amplitudes $A_k$, as defined in Equation 1 and expressed as a function of frequency rather than index k, and FIG. 5 shows the detailed region around 930 wavenumbers. Just as in FIGS. 2 and 3, because the oscillator amplitude spectra are representative of the bulk properties of the layer material, and are independent of the layer thickness or substrate, the spectra in FIGS. 4 and 5 are nearly identical for the two layers.

Figure 13:
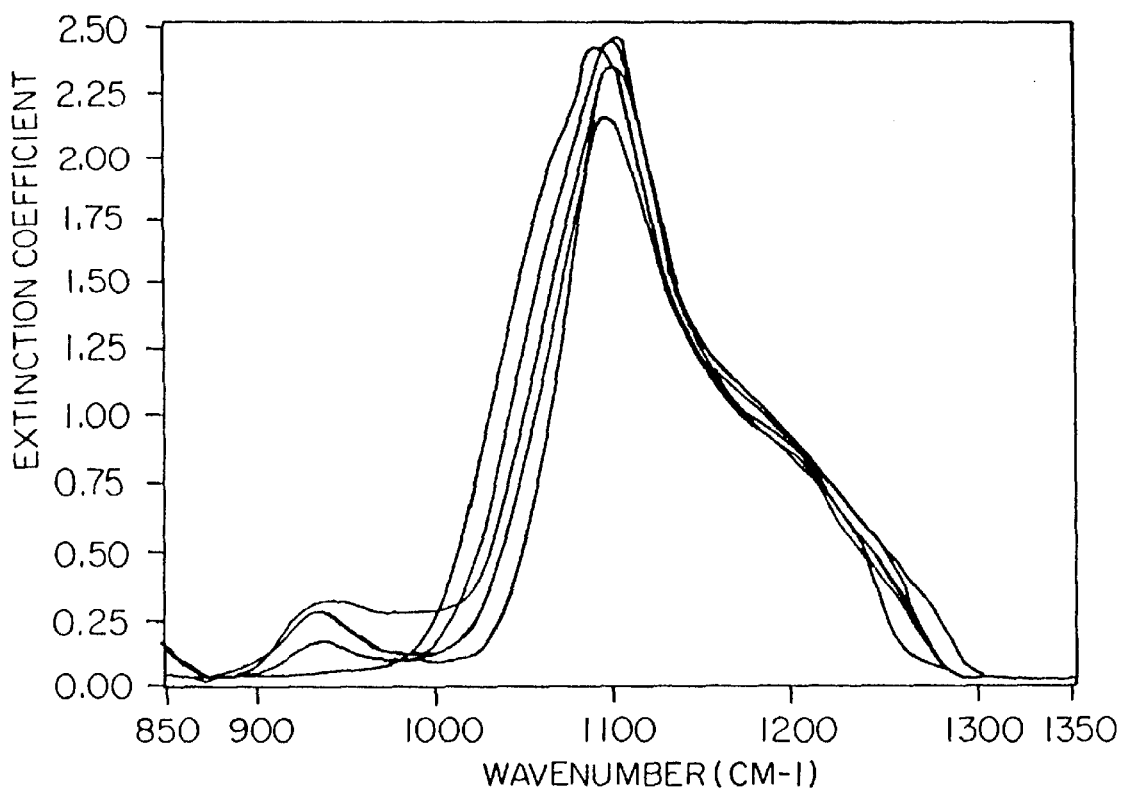
FIG. 13 is a plot of curves showing measurements of dielectric functions of fluorine-doped silica glass films used in training data set to generate loading vectors and a predictive model for fluorine concentrations; the data range from 600 nm to 1000 nm in thickness, and from zero to 8 weight percent fluorine.
Figure 14:
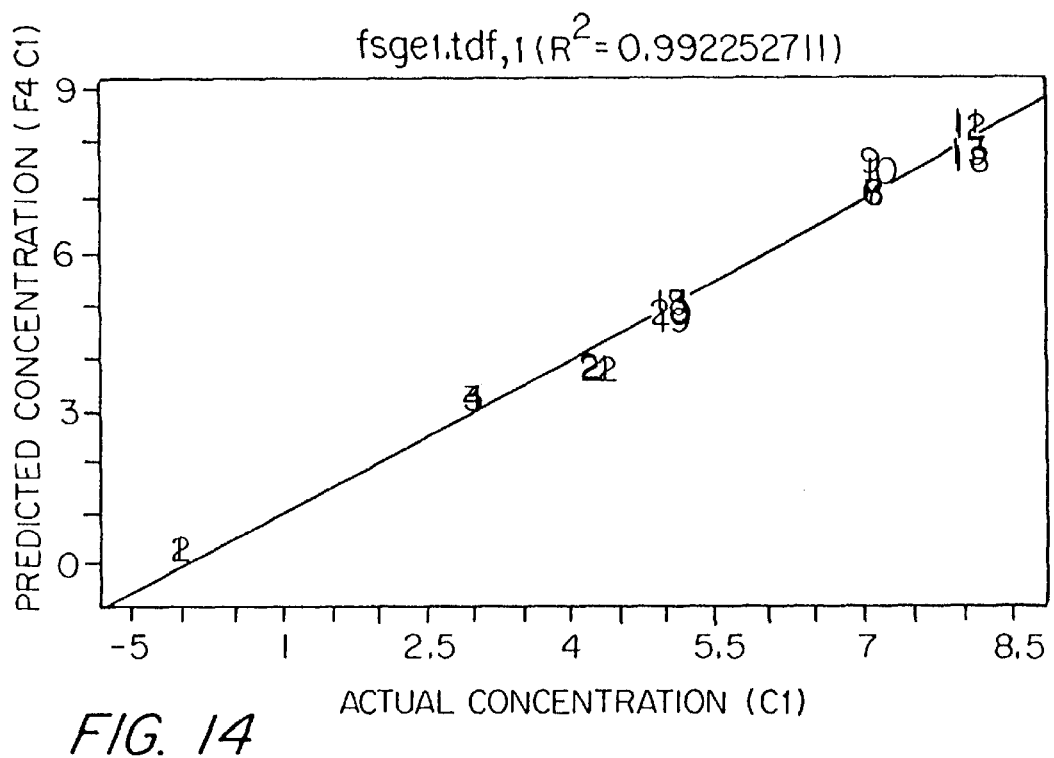
FIG. 14 is a cross-validation plot of fluorine concentration precision; the vertical axis represents the fluorine concentrations predicted via fitting of loading vectors to the dielectric functions of samples, extracted from infrared data, and the horizontal axis represents nominal concentrations measured independently and used to calibrate the predictive model.

The fluorine concentration was determined using one of several methods, such as a chemometric calibration of the dielectric functions or $A_k$ spectra in the vicinity of the 930 wavenumber absorption, or a simple peak height or peak area analysis of the 930 wavenumber feature. To perform the detailed quantitative measurement of the fluorine concentration, a statistical empirical model was created using a calibration sample set of independently analyzed composition. A set of dielectric function data, expressed as absorption coefficients for a training set of FSG films, is shown in FIG. 13. A cross-validation plot for this sample set (FIG. 14) demonstrates the efficacy of the method to correctly predict the fluorine concentrations of the samples in the training set. In this Example, four loading vectors we needed to span the training set.

EXAMPLE FOUR

Figure 6:
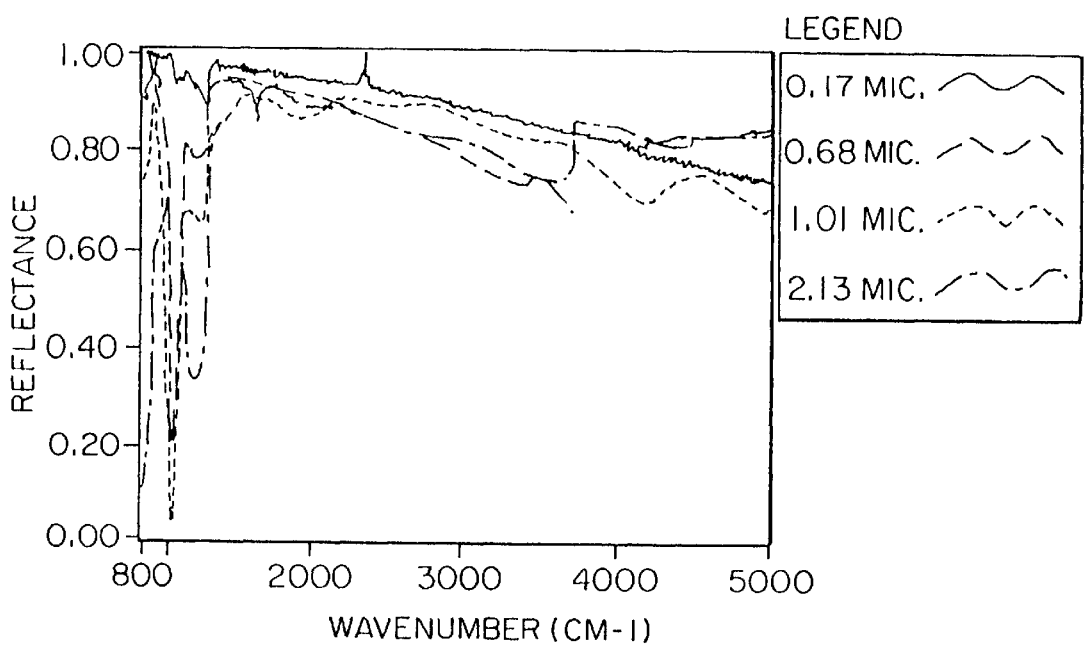
FIG. 6 is a plot of curves showing reflectance of four silicon dioxide layers, deposited on metal, ranging in thickness from 0.17 µm to 2.13 µm.
Figure 7:
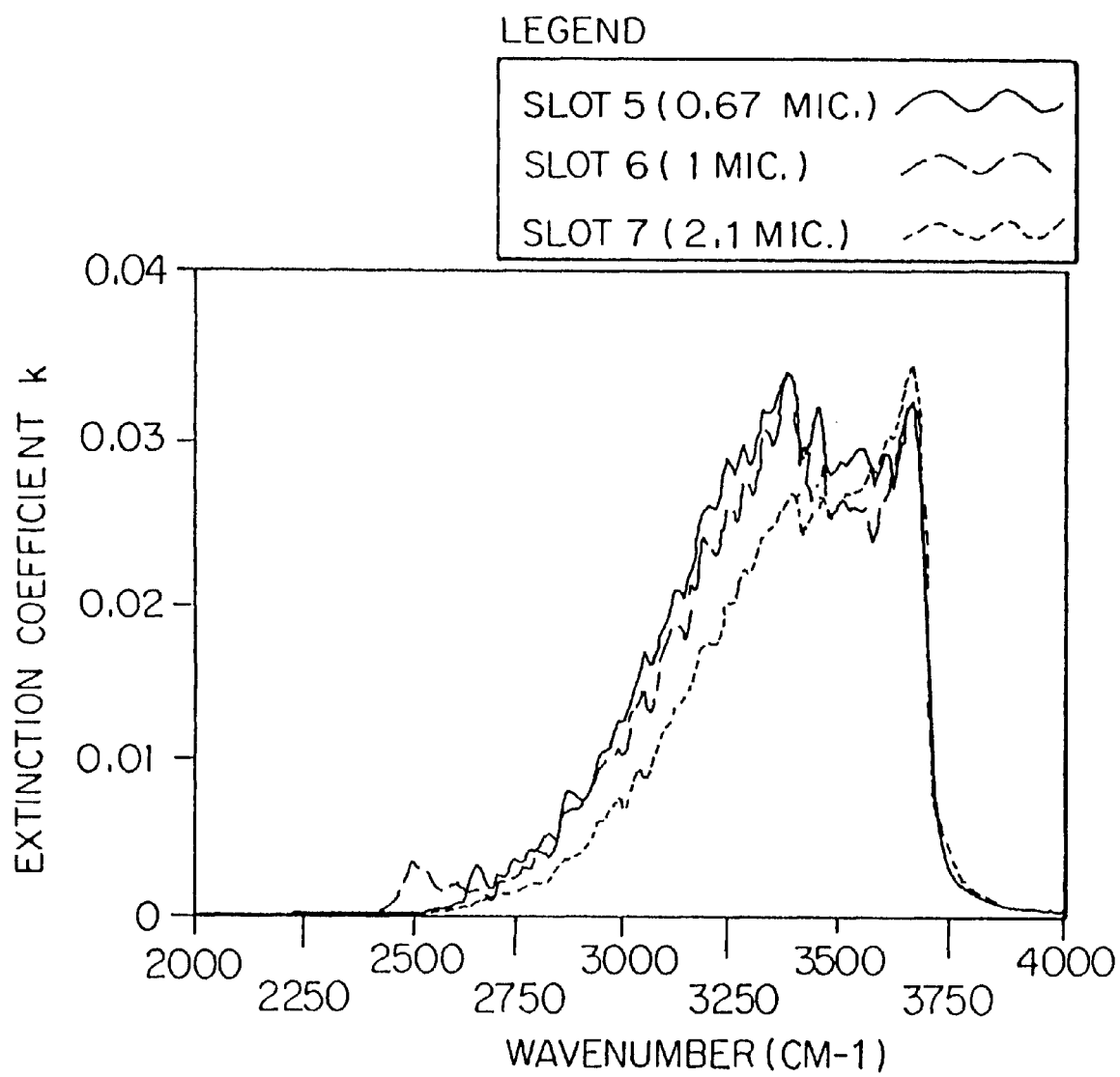
FIG. 7 is a plot of curves showing extinction coefficients k in the —OH absorption region, from which it can be seen that the 2.13 µm film has a smaller hydroxyl group absorption band than the two other films.

Analysis of Moisture and Bonded Hydroxyl Groups in Deposited Silicon Oxide Layers This Example illustrates the application of the present method for monitoring the hydroxyl group impurity levels in a dielectric film. FIG. 6 shows the measured infrared reflectance of four silicon dioxide layers deposited on metallized substrates, the thicknesses of the layers being 0.17 $\mu$m, 0.68 $\mu$m, 1.01 $\mu$m and 2.13 $\mu$m. Although features associated with the —OH and moisture absorption bands at about 3500 cm$^{-1}$ are visible in the reflectance curves, confounding effects of the thin film interference fringe make it difficult to estimate the moisture level from these spectra. FIG. 7 shows the extinction spectra k of the three thickest films in the region where —OH groups absorb strongly, extracted using the method of Morrison et al. The data clearly show the 2.13 micron film to have the smallest absorption band, and therefore the lowest concentration of —OH groups dispersed in the layer. To provide a quantitative analysis of the hydroxyl group and water concentrations, a statistical empirical chemometric model would be constructed (using step (c)) from a sample set covering the approximate range of moisture and —OH concentrations expected in the measurements. An unknown sample measurement would then be fit to the empirical model to provide the —OH concentration of the layer.

Figure 8A:
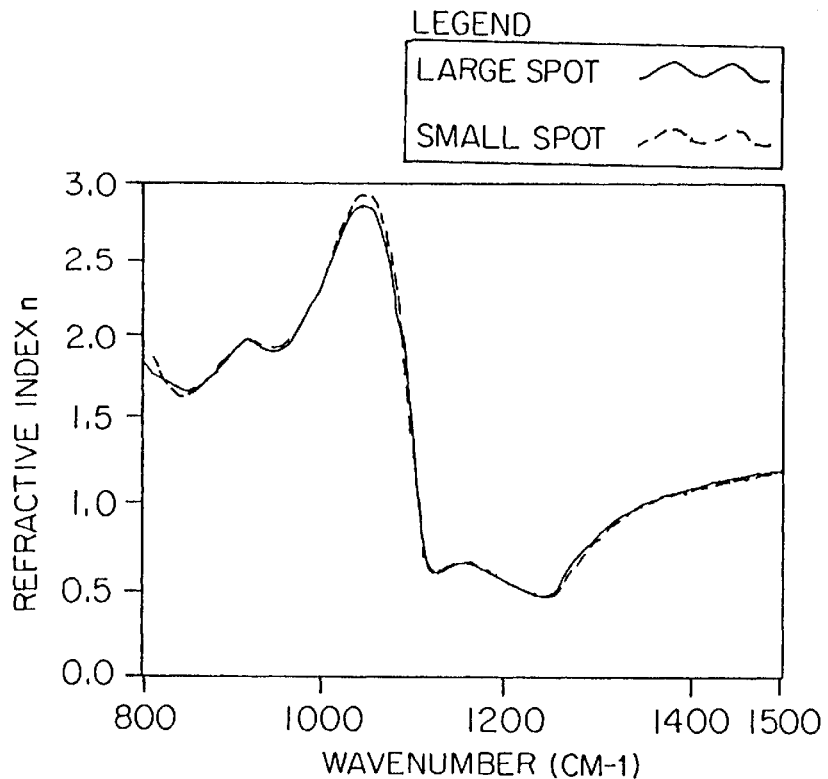
FIG. 8 comprises plots of curves showing dielectric functions extracted for the same silicon dioxide film on two different systems, namely, a large spot (5 mm), 10° angle of incidence system and a small spot (28 µm), 23° angle of incidence system, wherein plot (a) shows the refractive indices n and plot (b) shows the extinction coefficients k.
Figure 8B:
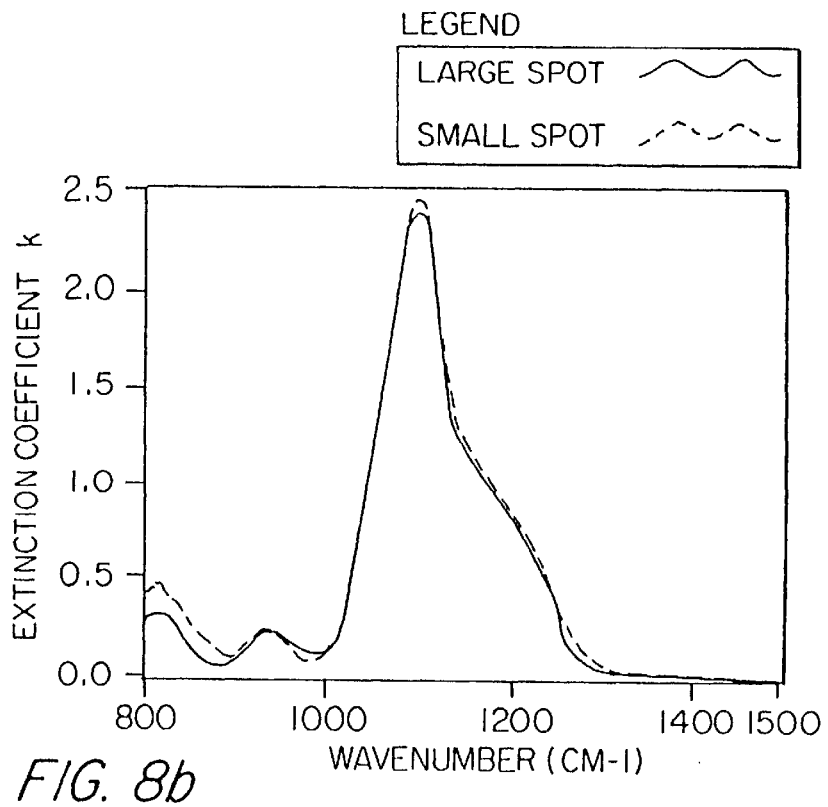

Because the algorithms relate the composition to the DF (a bulk layer property), rather than to the reflectance directly, the chemometric calibrations can be transferred readily from one system to another, even when gross differences exist in the measurement geometry. FIG. 8 shows dielectric function data extracted from the same sample using measurements from two very different systems, and illustrates this feature. The first system is a near normal (10°) incidence system with a 5 mm measurement, and the second is a small (28 micron) spot system with an average angle of incidence of 23°. The similarity of the two superimposed dielectric function spectra illustrates the ability of the present method to eliminate effects of machine-related structure from the reflectance data. This machine-independent characteristic of the method allows the use of reflection, emission, or ellipsometric data to compute layer properties, independently of the method used to generate the calibration model.

EXAMPLE FIVE

Analysis of Photoresist Chemistry

Organic photoresist thin films are commonly used in the semiconductor and related industries for the lithographic transfer, to substrates and thin films, of patterns having microscopic features. As the industry moves to incorporate into semiconductor devices features having dimensions of 0.25 micron and smaller, new classes of photoresists, which are sensitive to shorter wavelengths of light, are being employed. These so-called "chemically amplified photoresists," or "CARs," in which an annealing step (post exposure bake, or PEB) is performed after exposure, have relatively complex chemistries. During the PEB, the thickness of such a photoresist film is seen to decrease and subtle changes in the DF of the layer can also be observed, the latter being relatable to the chemical reactions that occur in the process. A method to monitor such chemical changes, which discriminates them from changes caused by film shrinkage, is therefore needed.

Infrared spectroscopy is an ideal technique for probing such a process because much of the relevent chemical information is encoded in the infrared absorption bands. Using a combination of sample model-based analysis and DF analysis, the chemical information can be decoded and differentiated from film thickness-related interference fringes. In the present Example a novel model-based synthetic differencing technique is used to accentuate features that are attributable to chemical reactions.

The IR reflectance of photoresist films, subjected to various levels of exposure, was measured in the range 800–5000 cm$^{-1}$ (12.5–2 $\mu$m), at an average angle of incidence of 23° from the surface normal. The sensitivity of the IR dielectric function to thin-film chemistry is well illustrated for the case of photoresist analysis. Chemically amplified resists are known to undergo key catalytic reactions during a post-exposure bake, which reactions depend not only upon the bake conditions but also upon the exposure dose and the chemical composition of the photoresist resin.

Figure 9A:
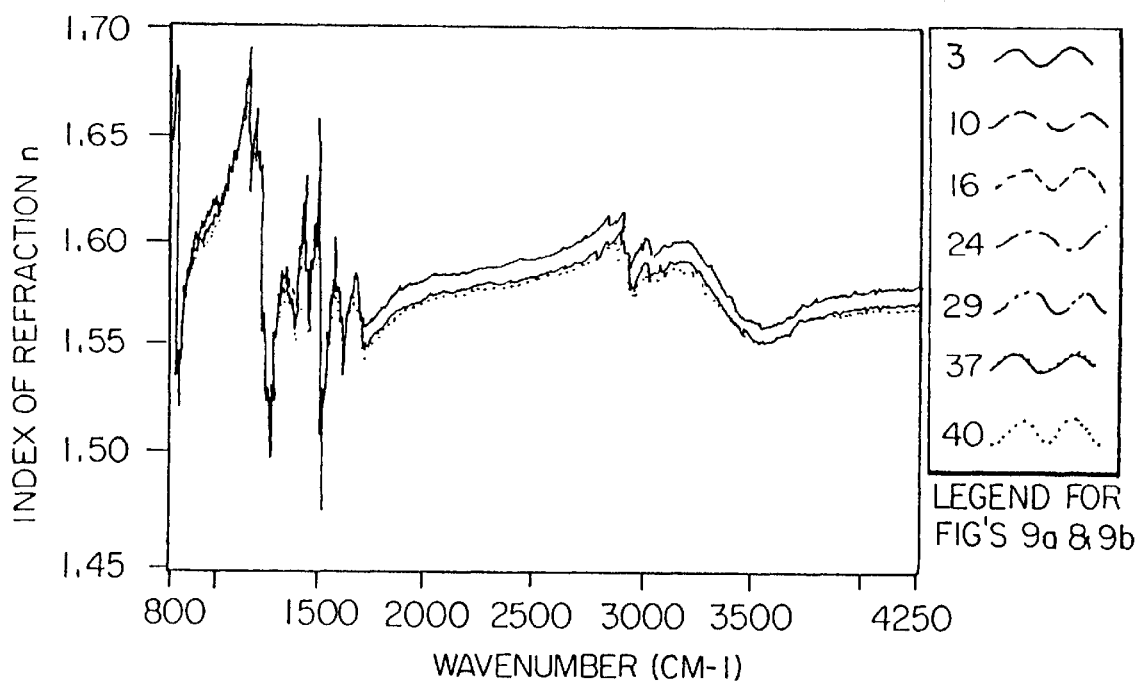
FIG. 9 comprises plots of curves showing (a) the extracted indices of refraction and (b) extinction coefficients for a UV5 resist, determined as a function of exposure level.
Figure 9B:
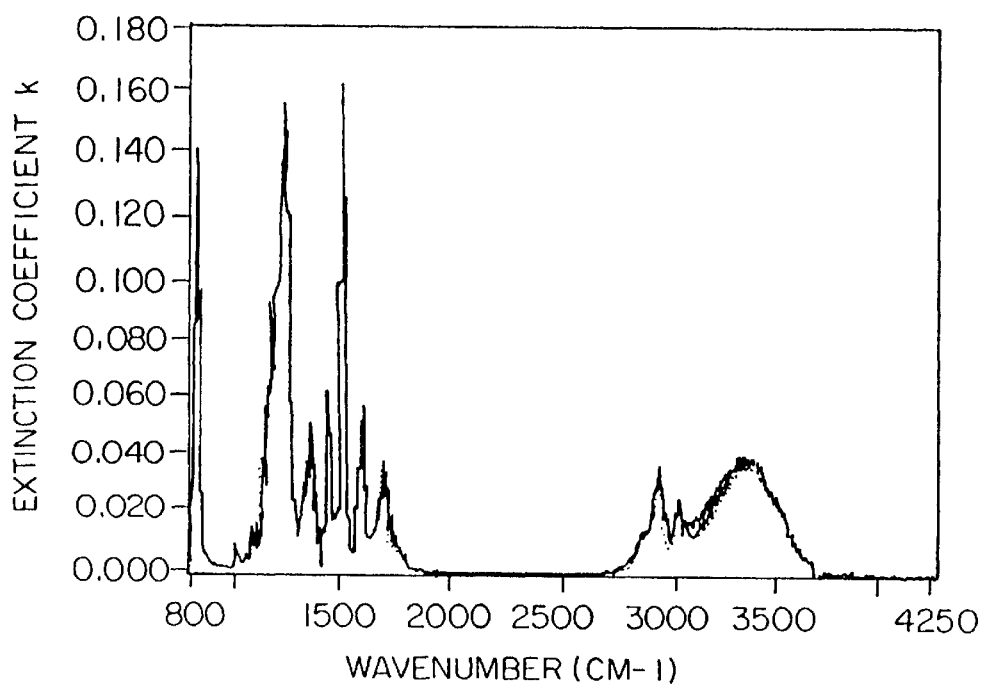
Figure 10A:
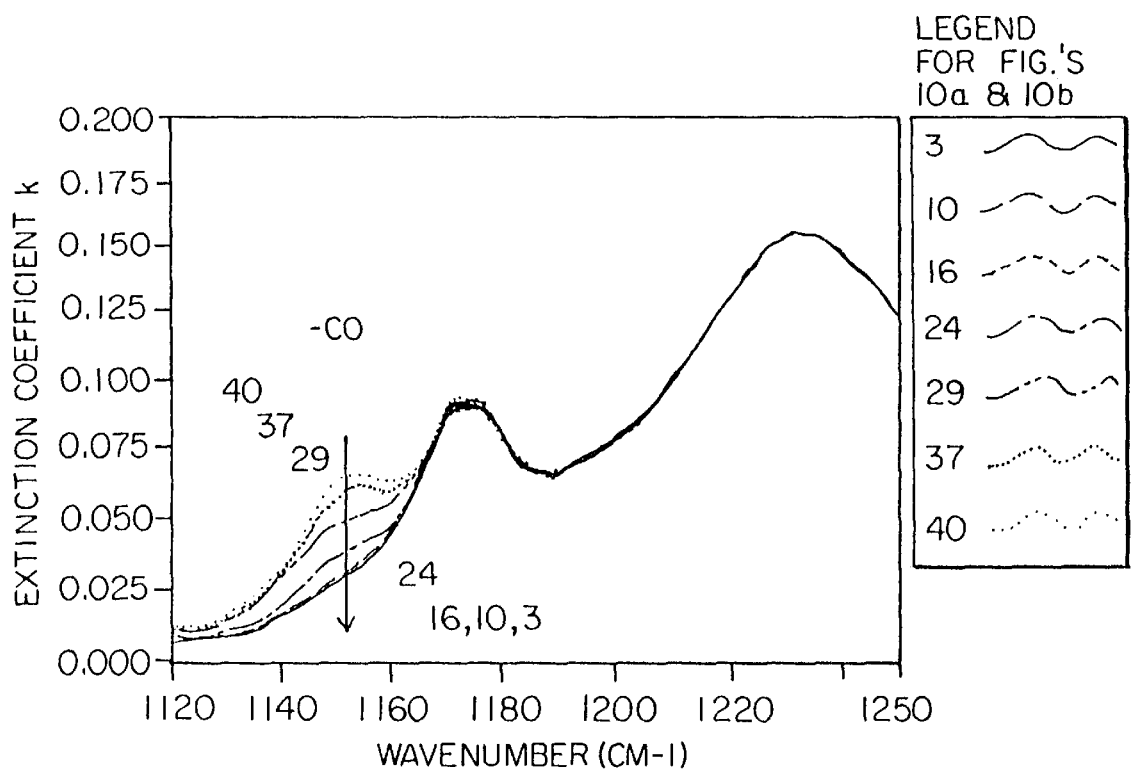
FIG. 10 comprises plots of curves showing an expanded view of the spectral regions over which the photoresist DF varied with exposure after the post-exposure bake.
Figure 10B:
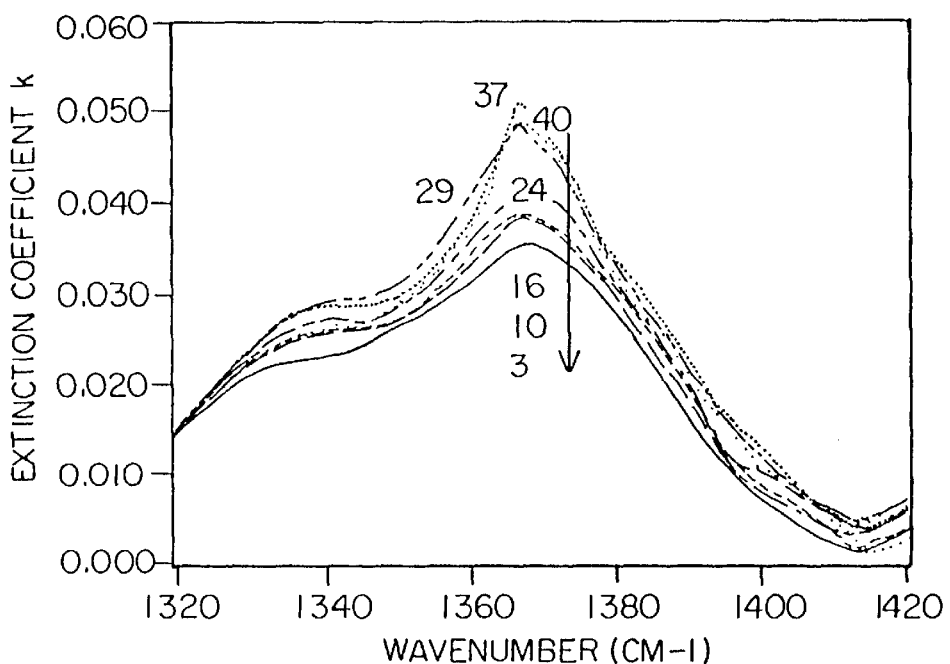
Figure 10C:
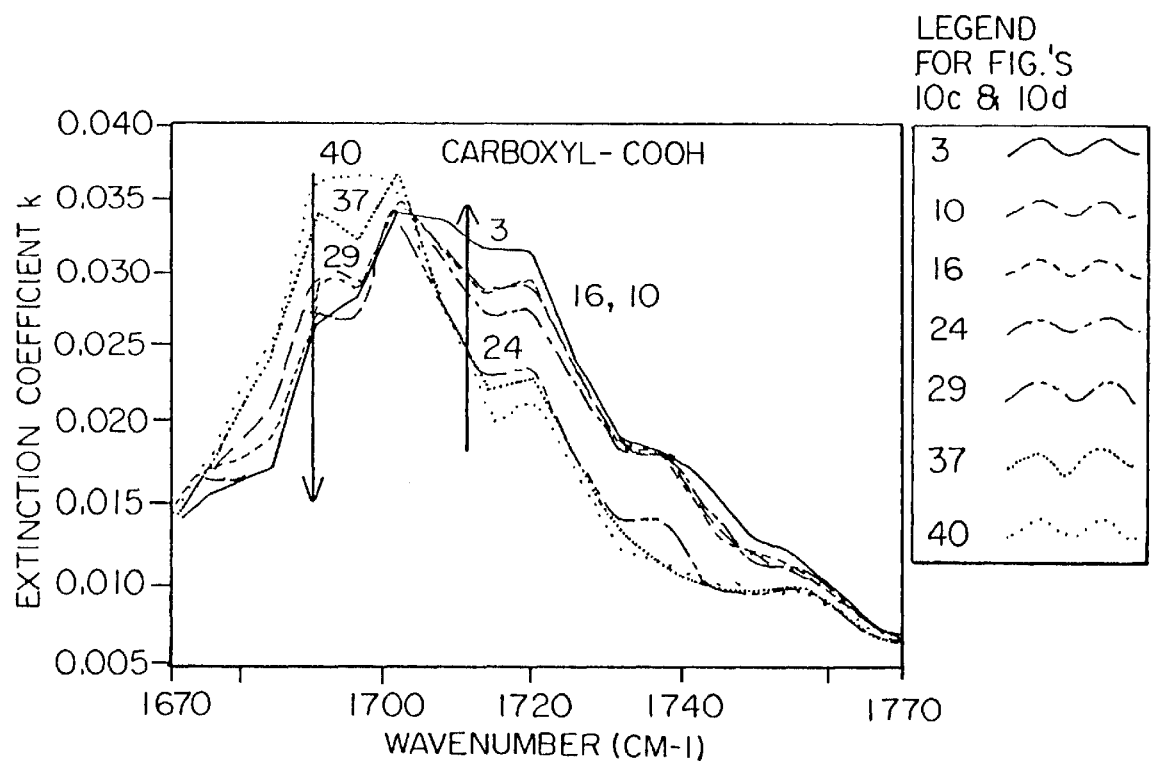
Figure 10D:
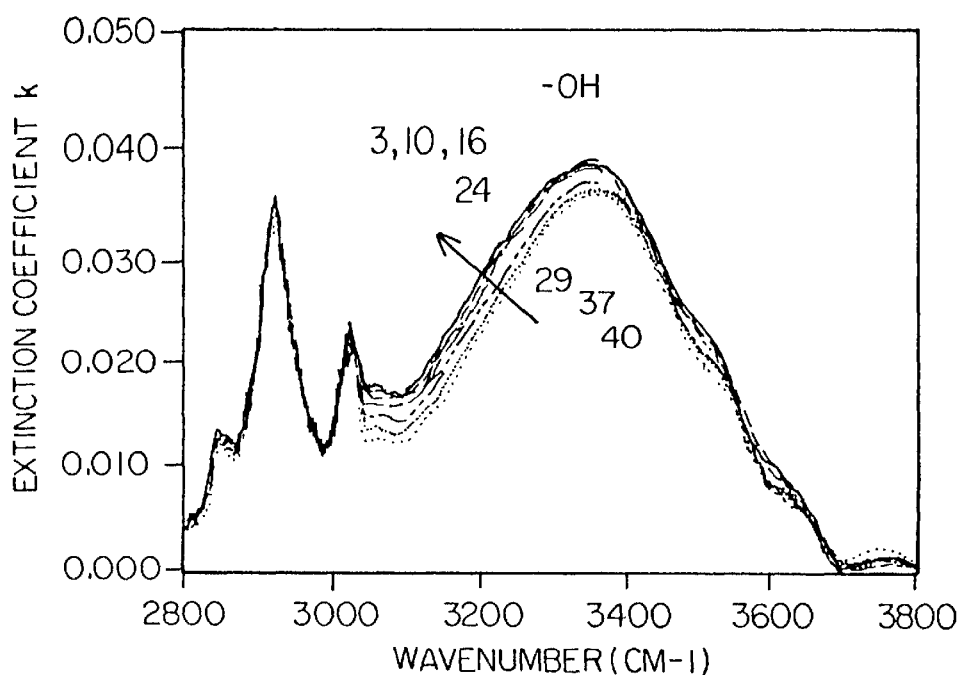

FIG. 9 shows the extracted dielectric function for a CAR layer (UV5) subjected to a range of exposure doses ranging from unexposed through doses significantly higher than those employed for the nominal exposure process, and being represented as the index of refraction n and the absorption index k and expressed as functions of wavenumber; FIG. 10 shows, in greater detail, specific regions that changed as a function of exposure dose, and in both FIGS. 9 and 10 the exposure dose decreased as the curve labels increased. The data show a great deal of structure that can be related to the various carbon-based and —OH functional groups. At various levels of exposure the sample resist shows, very clearly, systematic variations in chemistry as well as changes in indices. The Figures also show that only limited regions of the spectral range change with exposure. In particular, the reduction of the band around 1150 cm$^{-1}$ corresponds to —CO groups reacting to produce —OH groups, the increase of which is visible in the 3100–3500 cm$^{-1}$ region. Changes in the 1700 cm$^{-1}$ region have been attributed to the deprotection reaction involving ester bonds reacting with the photo-generated acid, to yield carboxylic acids. Finally, it is noted that a method such as PCA, which is capable of isolating the minimum degrees of freedom needed to span the sample variation, could greatly reduce the computational complexity involved in modeling the reflectance of these materials.

Thus, it can be seen that the foregoing and related objects of the invention are readily attained by the practice of the method of the instant invention, and by the provision of apparatus for implementing the method.

Having thus described the invention, what is claimed is:

1. A method for estimating at least one parameter of a sample, determined from the dielectric function of a material of which at least one layer of the sample consists, comprising the steps:
   (a) providing a sample comprised of at least one layer and having a substantially specular surface;
   (b) defining an optical model of said sample along a direction perpendicular to said surface and based upon reflectance values, said at least one layer being defined in said model by a thickness value and, for each of a multiplicity of wavelengths in the infrared spectral region, by a dielectric function value;
   (c) providing a traing set consisting of measured values of said at least one parameter and an associated dielectric function, said measured values being obtained from a multiplicity of samples selected to represent a range of values of said at least one parameter;
   (d) determining from said traing set a predictive mathematical relationship between said at least one parameter and said associated dielectric function, so as to enable prediction of said at least one parameter from input values of dielectric function;
   (e) irradiating said specular surface of said sample with infrared radiation, including said multiplicity of wavelengths, and obtaining a measured reflectance spectrum composed of values obtained over said multiplicity of wavelengths;
   (f) simulating a reflectance spectrum from said optical model at said multiplicity of wavelengths using values of said dielectric function calculated from assumed dielectric function descriptors and a value of said thickness of said at least one layer, and computing said various values of said dielectric function descriptors so as to minimize the difference between said simulated reflectance spectrum and said measured reflectance spectrum, thereby determining an optimized dielectric function value for said at least one layer at said multiplicity of wavelengths; and
   (g) calculating the value of said at least one parameter using said optimized dielectric function value and said predictive mathematical relationship.

2. The method of claim 1 wherein a pattern of variation derived from said training set is utilized so as to constrain the number of said descriptors required to describe said dielectric function.

3. The method of claim 2 wherein said values of dielectric function used are parametrized as weighted linear superpositions of vectors determined to span the space of dielectric functions derived from said training set, and wherein said descriptors are the coefficients of said vectors.

4. The method of claim 3 in which at least one of said vectors is determined through a multivariate statistical regression of the set of dielectric functions measured in creating said training set.

5. The method of claim 1 wherein said predictive mathematical relationship is determined through a multivariate statistical regression of said training set.

6. The method of claim 1 wherein said predictive mathematical relationship is determined employing a neural network algorithm calibrated with said training set.

7. The method of claim 1 wherein said predictive mathematical relationship is determined by establishing a library of dielectric function values with associated values of said at least one parameter, organized in the form of a look-up table, and wherein said look-up table is accessed to determined said parameter from said optimized values.

8. The method of claim 7 wherein said look-up table access includes the additional step of interpolating between elements of said look-up table.

9. The method of claim 1 wherein said predictive mathematical relationship is established between said at least one parameter and spectral features derived from the dielectric function of said training set.

10. The method of claim 9 wherein said spectral feature is at least one characteristic of at least one peak observed in said training set dielectric function.

11. The method of claim 10 wherein said at least one characteristic is the intensity, position, height or width of said at least one peak.

12. The method of claim 1 wherein said thickness value is varied in said step (f).

13. The method of claim 1 wherein said at least one parameter represents at least one of the species and the concentration of at least one chemical constituent of said material of said at least one layer.

14. The method of claim 13 in which said at least one parameter is the concentration of fluorine atoms within said material of said at least one layer.

15. The method of claim 13, wherein said at least one parameter is the concentration of hydroxyl groups within a dielectric matrix.

16. The method of claim 13 wherein said at least one parameter is the concentration of water molecules within a dielectric matrix.

17. The method of claim 13 wherein said at least one parameter is the concentration of hydrogen atoms within a dielectric matrix.

18. The method of claim 13 wherein said at least one parameter is the concentrations of at least one of boron, phosphorus, and germanium in said at least one layer.

19. The method of claim 13 wherein said at least one layer contains at least one of the species barium, strontium and titanium atoms, and wherein said at least one parameter is the concentration of said at least one species atom therein.

20. The method of claim 1 wherein said at least one parameter represents the stress in said at least one layer.

21. The method of claim 1 wherein said at least one parameter represents the density of crystal defects in said at least one layer.

22. The method of claim 1 wherein said at least one parameter represents a porosity characteristic of said at least one layer.

23. The method of claim 22 wherein said porosity characteristic describes the pore size distribution within said at least one layer.

24. The method of claim 22 wherein said porosity characteristic describes the total fractional pore volume within said at least one layer.

25. The method of claim 1 wherein said at least one parameter is characteristic of a lithography process, and wherein said at least one layer comprises a lithographic resist layer.

26. The method of claim 25 wherein said at least one parameter represents the exposure dose of said lithographic resist layer.

27. The method of claim 25 wherein said at least one parameter represents the critical dimension obtained after completing a lithography process step on said sample.

28. The method of claim 13 wherein said at least one parameter is a measure of the sidewall profile obtained after completing a lithography process step on said sample.

29. The method of claim 13 wherein said at least one layer is a compound semi-conductor composed of at least three chemical elements, and wherein said at least one parameter is representative of the relative ratios of said at least three chemical elements.

30. The method of claim 29 wherein said elements are selected from the group consisting of Si, Ge, Al, Ga, As, N, P, In, C, Sb, Zn, Hg, Cd, B, and Te.

31. The method of claim 1 wherein said at least one parameter is representative of the electrical dielectric constant of said at least one layer.

32. Apparatus for estimating at least one parameter of a sample, determined from the dielectric function of a material of which at least one layer of the sample consists, comprising: means for irradiating a surface of a sample with infrared radiation, including each of multiplicity of wavelengths in the infrared spectral region, and for obtaining a measured reflectance spectrum composed of values obtained over said multiplicity of wavelengths; and electronic data processing means, said data processing means being programmed to:

(a) define an optical model of the sample along a direction perpendicular to a surface thereof and based upon reflectance values, the at least one layer of the sample being defined in said model by a thickness value and, for each of a multiplicity of wavelengths in said infrared spectral region, by a dielectric function value;

(b) provide a training set consisting of measured values of said at least one parameter and an associated dielectric function, said measured values being obtained from a multiplicity of samples selected to represent a range of values of said at least one parameter;

(c) determine from said training set a predictive mathematical relationship between said at least one parameter and said associated dielectric function, so as to enable prediction of said at least one parameter from input values of dielectric function;

(d) simulate a reflectance spectrum from said optical model at said multiplicity of wavelengths using values of said dielectric function calculated from assumed dielectric function descriptors and a value of said thickness of said at least one layer, and to compute the values of said dielectric function descriptors so as to minimize the difference between said simulated reflectance spectrum and said measured reflectance spectrum, thereby determining an optimized dielectric function value for said at least one layer at said multiplicity of wavelengths; and (e) calculate the value of said at least one parameter using said optimized dielectric function value and said predictive mathematical relationship.

* * * * *